United States Patent
Der et al.

(10) Patent No.: US 10,723,990 B2
(45) Date of Patent: Jul. 28, 2020

(54) FLEXIBLE FILM IN SINGLE USE BIOREACTOR

(71) Applicant: EMD Millipore Corporation, Burlington, MA (US)

(72) Inventors: Kara Der, Burlington, MA (US); Anne Hansen, Burlington, MA (US); James McSweeney, Burlington, MA (US); David Kraus, Burlington, MA (US); Jeffrey Pearsons, Burlington, MA (US); Amy Wood, Burlington, MA (US)

(73) Assignee: EMD Millipore Corporation, Burlington, MA (US)

( * ) Notice: Subject to any disclaimer, the term of this patent is extended or adjusted under 35 U.S.C. 154(b) by 244 days.

(21) Appl. No.: 14/782,487

(22) PCT Filed: Mar. 17, 2014

(86) PCT No.: PCT/US2014/030140
§ 371 (c)(1),
(2) Date: Oct. 5, 2015

(87) PCT Pub. No.: WO2014/172047
PCT Pub. Date: Oct. 23, 2014

(65) Prior Publication Data
US 2016/0040113 A1  Feb. 11, 2016

Related U.S. Application Data

(60) Provisional application No. 61/813,726, filed on Apr. 19, 2013.

(51) Int. Cl.
*C12M 1/00* (2006.01)
*B01F 15/00* (2006.01)
(Continued)

(52) U.S. Cl.
CPC ............ *C12M 27/20* (2013.01); *B01F 7/021* (2013.01); *B01F 13/0872* (2013.01);
(Continued)

(58) Field of Classification Search
CPC .............................. C12M 23/14; C12M 23/28
See application file for complete search history.

(56) References Cited

U.S. PATENT DOCUMENTS

| 1,940,752 A | 12/1933 | Holmquist |
| 3,753,492 A | 8/1973 | Aiello et al. |

(Continued)

FOREIGN PATENT DOCUMENTS

| CN | 1358562 A | 7/2002 |
| CN | 201012323 Y | 1/2008 |

(Continued)

OTHER PUBLICATIONS

Chinese communication, with English translation, dated Sep. 2, 2016 in corresponding Chinese patent application No. 201480022165.7.

(Continued)

*Primary Examiner* — Jonathan M Hurst
(74) *Attorney, Agent, or Firm* — Nields, Lemack & Frame, LLC (57) ABSTRACT

A container, such as a disposable or single use bioreactor, optionally having one or more inlets and one or more outlets and a mixer associated with the container to cause mixing, dispersing, homogenizing and/or circulation of one or more ingredients contained or added to the container. The container includes a flexible baffle shaped and positioned within the container to improve mixing, particularly to improve low shear mixing. The baffle is positioned within the container so as to disrupt the vortex formed by the mixer, or prevent formation of a vortex. The baffle is shaped with both (Continued)

horizontal and vertical elements to enhance disruption of the vortex across the entire vessel height and provide homogeneous mixing throughout all operating volumes. In certain embodiments, the baffle is X-shaped.

15 Claims, 6 Drawing Sheets (51) Int. Cl.
*C12M 1/06* (2006.01)
*B01F 7/02* (2006.01)
*B01F 13/08* (2006.01)
*C12M 1/12* (2006.01)

(52) U.S. Cl.
CPC .... *B01F 15/0085* (2013.01); *B01F 15/00915* (2013.01); *C12M 23/22* (2013.01); *C12M 23/26* (2013.01); *C12M 23/28* (2013.01); *C12M 25/16* (2013.01); *C12M 27/02* (2013.01)

(56) References Cited

U.S. PATENT DOCUMENTS

| | | | |
|---|---|---|---|
| 3,813,086 | A | 5/1974 | Ebner et al. |
| 3,865,721 | A | 2/1975 | Kaelin |
| 4,335,215 | A * | 6/1982 | Tolbert ................ C07K 14/555 435/403 |
| 4,519,959 | A | 5/1985 | Takeuchi et al. |
| 4,699,740 | A | 10/1987 | Bollenrath |
| 4,896,971 | A | 1/1990 | Weetman et al. |
| 4,934,828 | A * | 6/1990 | Janssen ................ B01F 7/1675 366/307 |
| 5,203,630 | A | 4/1993 | Howk |
| 5,356,600 | A | 10/1994 | Kiyonaga et al. |
| 5,358,332 | A | 10/1994 | Derksen et al. |
| 5,492,408 | A | 2/1996 | Alfare |
| 5,620,252 | A | 4/1997 | Maurer |
| 5,758,965 | A | 6/1998 | Gambrill et al. |
| 6,250,797 | B1 | 6/2001 | Weetman |
| 6,508,583 | B1 | 1/2003 | Shankwitz et al. |
| 6,854,877 | B2 | 2/2005 | Hoobyar et al. |
| 7,168,848 | B2 | 1/2007 | Gigas et al. |
| 8,057,092 | B2 | 11/2011 | Ryan et al. |
| 8,323,958 | B2 | 12/2012 | Woods et al. |
| 2004/0165477 | A1 | 8/2004 | Long |
| 2005/0213428 | A1 | 9/2005 | Freude et al. |
| 2005/0249033 | A1 | 11/2005 | Krause |
| 2005/0272146 | A1 | 12/2005 | Hodge et al. |
| 2007/0036027 | A1 | 2/2007 | Meier |
| 2007/0091716 | A1 | 4/2007 | Zeikus |
| 2007/0289206 | A1 | 12/2007 | Kertz |
| 2008/0131957 | A1 | 6/2008 | Ryan et al. |
| 2010/0015696 | A1 | 1/2010 | Claes et al. |
| 2010/0080077 | A1 | 4/2010 | Coy |
| 2011/0312087 | A1 | 12/2011 | Khan |
| 2012/0027324 | A1 | 2/2012 | Morrissey et al. |

FOREIGN PATENT DOCUMENTS

| | | |
|---|---|---|
| CN | 201500515 U | 6/2010 |
| CN | 202072696 U | 12/2011 |
| CN | 102513006 A | 6/2012 |
| CN | 103037959 A | 4/2013 |
| DE | 4235498 A1 | 4/1994 |
| DE | 202007005395 U1 | 7/2007 |
| DE | 102006020706 A1 | 11/2007 |
| EP | 0254826 A2 | 2/1988 |
| EP | 0727249 A1 | 8/1996 |
| EP | 0470493 B1 | 9/1996 |
| EP | 0873781 A1 | 10/1998 |
| EP | 1961806 A2 | 8/2008 |
| EP | 2039754 A1 | 3/2009 |
| EP | 2412428 A1 | 2/2012 |
| JP | 7-31134 U | 6/1995 |
| JP | 2008-501347 A | 1/2008 |
| JP | 2009072133 A | 4/2009 |
| KR | 2009-0029264 A | 3/2009 |
| KR | 101167083 B1 | 7/2012 |
| WO | 9322418 A1 | 11/1993 |
| WO | 2007134267 A2 | 11/2007 |
| WO | 2008040567 A1 | 4/2008 |
| WO | 2011/112680 A1 | 9/2011 |

OTHER PUBLICATIONS

Chinese communication, with English translation, dated May 12, 2017 in corresponding Chinese patent application No. 201480022165.7.
Japanese communication, with English translation, dated Jan. 4, 2017 in corresponding Japanese patent application No. 2016-508942.
Korean communication, with English translation, dated Jan. 31, 2017 in corresponding Korean patent application No. 10-2015-7028387.
Canadian communication dated Apr. 18, 2017 in corresponding Canadian patent application No. 2,908,806.
International Search Report and Written Opinion dated Aug. 12, 2014 in corresponding PCT application No. PCT/US2014/030140.
International Preliminary Report on Patentability dated Oct. 29, 2015 in corresponding PCT application No. PCT/US2014/030140.
Canadian communication dated Aug. 12, 2016 in corresponding Canadian patent application No. 2,908,806.
European communication dated Dec. 16, 2016 in corresponding European patent application No. 14785323.8.
Korean communication, with English translation, dated Nov. 29, 2017 in corresponding Korean patent application No. 10-2015-7028387.
Indian communication dated Mar. 12, 2019 in corresponding Indian patent application No. 9553/DELNP/2015.

* cited by examiner

FLEXIBLE FILM IN SINGLE USE BIOREACTOR

This application claims priority of U.S. Provisional Application Ser. No. 61/813,726 filed Apr. 19, 2013 the disclosure of which is incorporated herein by reference.

FIELD

Embodiments disclosed herein relate to a container useful as a bioreactor. In particular, embodiments disclosed herein include a flexible film baffle, which has both vertical and horizontal components when positioned in the container, particularly suited for use in a single use stirred tank bioreactor.

BACKGROUND

Traditionally, fluids have been processed in systems that utilize stainless steel containers. These containers are sterilized after use so that they can be reused. The sterilization procedures are expensive and cumbersome as well as being ineffectual at times.

In order to provide greater flexibility in manufacturing and reduce the time needed to effect a valid regeneration of the equipment, manufacturers have begun to utilize disposable sterilized containers such as bags that are used once with a product batch and then disposed.

An example of use of these disposable bags is in a system for mixing two or more ingredients, at least one of which is liquid and the other(s) being liquid or solid, and the bag has a mixing element or the like for causing the contents to mix as uniformly as possible.

For example, in the production of vaccines, the liquids involved often contain aluminum salt as an adjuvant. The aluminum salt improves the effectiveness of the vaccine by enhancing the body's immune response. Unfortunately, the aluminum salt has particles sizes larger than 0.2 µm, and thus sterile filtering generally is not an option. As a result, it is often advantageous to minimize the number of containers into which the vaccine needs to be transferred, since each transfer represents a potential breach of sterility, and the resulting contamination can't be filtered away. Accordingly, it is advantageous to be able to mix vaccines in the same container, such as a flexible, disposable bag, that they are shipped in.

Another example is a bioreactor or fermentor in which cells are either in suspension or on microcarriers and the bag has a circulating member for circulating the liquid, gases, and in some cases the cells around the interior of the bag.

Some conventional bioreactors include a sleeve to hold a rigid metal insert that acts as a baffle for improved mixing. However, large volume bioreactors, e.g., 1000 L and 2000 L volume bioreactors, present challenges for implementing such a rigid baffle, since the increased height of these systems makes it difficult to introduce the rigid insert through the top of the bioreactor. In addition, the bottom to top mixing seen in the smaller scales becomes even more pronounced as the overall height of the bioreactor increases, even with the reduced height to width aspect ratios.

Good mixing is critical, for optimization of a bioreactor process. A well-designed mixing system provides three basic functions: creation of constant living conditions (nutrients, pH, temperature, etc.) in a homogeneous distribution; dispersion of gas for supplying $O_2$ and extracting $CO_2$; and optimization of heat transfer. Providing acceptable mixing, without imparting damaging shear effects, becomes more challenging as the scale of the bioreactor container increases. Some commercial bioreactor platforms include a single bottom mounted impeller. The formation of a vortex, with stagnant zones, is often associated with this single agitator. A baffle can be added to suppress vortex formation and provide for movement of the fluid into a preferred flow pattern of axial and radial flow. The inclusion of a well-designed baffle will allow for better mixing efficiency without the added high shear risk associated with multiple impellers and/or high impeller speeds.

It therefore would be desirable to provide a disposable or single use container for fluids with an improved baffle system to achieve homogeneous mixing necessary for optimal cell culture growth performance in bioreactors.

SUMMARY

In accordance with certain embodiments, disclosed herein is a container, such as a disposable or single use container, optionally having one or more inlets and one or more outlets and a mixer associated with the container to cause mixing, dispersing, homogenizing and/or circulation of one or more ingredients contained or added to the container. In accordance with certain embodiments, the container includes a flexible baffle shaped and positioned within the container to improve mixing, particularly to improve low shear mixing. In accordance with certain embodiments, the baffle is positioned within the container so as to disrupt the vortex formed by the mixer, or prevent formation of a vortex. In accordance with certain embodiments, the baffle is used with a single impeller to limit shear effects. In accordance with certain embodiments, the baffle is shaped with both horizontal and vertical elements to enhance disruption of the vortex across the entire vessel height and provide homogeneous mixing throughout all operating volumes. In accordance with certain, embodiments, the baffle is X-shaped.

Also disclosed is a system for mixing a fluid in a container having an internal volume, the system comprising a container, an impeller assembly, a drive for the impeller assembly, and a baffle positioned within the container internal volume to break, prevent or minimize formation of any vortex formed during mixing.

Also disclosed is a method of mixing a fluid in a container with an impeller assembly and a baffle positioned in the container to break, prevent or minimize the formation of any vortex formed during mixing. In accordance with certain embodiments, the method includes introducing a fluid into a container, wherein an impeller assembly is at least partially contained in and is sealed in the container, and driving the blades or vanes of the impeller assembly to agitate the fluid in the bag. The baffle in the container breaks any vortex that may be formed by the rotating blades, or prevents or minimizes the formation of any vortex. In certain embodiments, the driver for the impeller assembly is external to the bag, and drives the impeller assembly magnetically.

Embodiments disclosed herein result in a homogeneous mixing state provided by the baffle and can provide even distribution of support matrices for adherent cells, such as microcarriers, increasing potential for good growth of certain cells, including, but not limited to stem cells. A good distribution of microcarriers can be obtained at lower power inputs, reducing shear level in the system and so reducing risks of damage to microcarriers and/or displacement of cells off carriers.

For certain processes or cell lines with increased sensitivity to shear, overall power input can be reduced while still maintaining good mixing. Lower power input translates to lower shear. This provides a good solution for extreme processes, i.e., processes requiring lower power input. With more homogeneous mixing at lower power input, a larger process window for cell culture processes is provided, providing greater flexibility in finding optimum process conditions. For processes designed to achieve high cell densities, good mixing can be obtained without the need for increase in power input.

Mixing times under 30 seconds (for 1000 L and below) for the nominal condition of 14 W/m$^3$ can be achieved.

DETAILED DESCRIPTION

In accordance with certain embodiments, the disposable container designed to receive and hold a fluid can be formed of monolayer or multilayer flexible walls formed of a polymeric composition such as polyethylene, including ultrahigh molecular weight polyethylene, linear low density polyethylene, low density or medium density polyethylene; polypropylene; ethylene vinyl acetate (EVOH); polyvinyl chloride (PVC); Polyvinyl acetate (PVA); ethylene vinyl acetate copolymers (EVA copolymers); blends of various thermoplastics; co-extrusions of different thermoplastics; multilayered laminates of different thermoplastics; or the like. By "different" it is meant to include different polymer types such as polyethylene layers with one or more layers of EVOH as well as the same polymer type but of different characteristics such as molecular weight, linear or branched polymer, fillers and the like. Typically medical grade and preferably animal-free plastics are used. They generally are sterilizable such as by steam, ethylene oxide or radiation such as beta or gamma radiation. Most have good tensile strength, low gas transfer and are either transparent or at least translucent. Preferably the material is weldable and is unsupported. Preferably the material is clear or translucent, allowing visual monitoring of the contents. The container can be provided with one or more inlets, one or more outlets and one or more optional vent passages. The container is of a sufficient size to contain fluid, such as cells and a culture medium, to be mixed. In certain embodiments, the container may be a bioreactor capable of supporting a biologically active environment, such as one capable of growing cells in the context of cell cultures.

In certain embodiments, the container may be a disposable, deformable, foldable bag that defines a closed volume, that is sterilizable for single use, capable of accommodating contents, such as biopharmaceutical fluids, in a fluid state, and that can accommodate a mixing device partially or completely within the interior of the container. In certain embodiments, the closed volume can be opened, such as by suitable valving, to introduce a fluid into the volume, and to expel fluid therefrom, such as after mixing is complete.

In certain embodiments, the container may be a two-dimensional or "pillow" bag, or it may be a three-dimensional bag. The particular geometry of the container is not particularly limited. In certain embodiments, the container may include a rigid base, which provides access points such as ports or vents. Each container may contain one or more inlets and outlets and optionally other features such as sterile gas vents and ports for the sensing of the liquid within the container for parameters such as conductivity, pH, temperature, dissolved gases and the like.

In certain embodiments each container contains, either partially or completely within its interior, an impeller assembly for mixing, dispersing, homogenizing, and/or circulating one or more liquids, gases and/or solids contained in the container. In accordance with certain embodiments, the impeller assembly may include one or more blades, which are movable, such as by rotation or oscillation about an axis. In certain embodiments, the impeller assembly converts rotational motion into a force that mixes the fluids it is in contact with. The impeller assembly may have a protective hood formed over at least a part of the blades with a space contained between the under surface of the hood and the outer dimension of the blades so as to allow for free movement of the blades and liquid between the blades and the under surface of the hood. The hood services to protect the container from the blades that could otherwise damage the container.

In accordance with certain embodiments, the container includes at least one baffle member, the baffle member being positioned in the container such that when the container contains fluid, the baffle member has both horizontal and vertical components submerged in the fluid. In accordance with certain embodiments, a portion less than the whole of the baffle member is not submerged in the fluid. In accordance with certain embodiments, the baffle extends to the inner radial dimensions of the container. In accordance with certain embodiments, the baffle member is X-shaped.

Proper design and implementation or the impeller/baffle combination provides a mixing solution across a wide range of volumes and aspect ratios, enabling the development of a family of bioreactor systems with excellent scalability and well-defined performance.

In accordance with certain embodiments, the baffle member is positioned in the container so that one leg of the "X" extends through the surface of the fluid near or at the location where the vortex would form upon actuation of the impeller assembly. This placement, having both a vertical and horizontal element of the baffle slicing through the fluid surface, acts as a vortex breaker, disrupting the circular flow path of the fluid. The X-shape, when compared to other configurations of strictly vertical or strictly horizontal baffles, allows for better disruption of flow paths within the bulk of the fluid, reducing the tendency for bottom to top mixing (with the impeller assembly located at the bottom of the container) and providing a more homogenous distribution within a shorter time period.

In accordance with certain embodiments, the baffle member should be wide enough (with respect to the radial dimension or the container) to disrupt the vortex formation at the surface of the fluid, but not too wide to block flow from side-to-side within the container, which would increase the time for mixing the entire volume.

Figure 1:
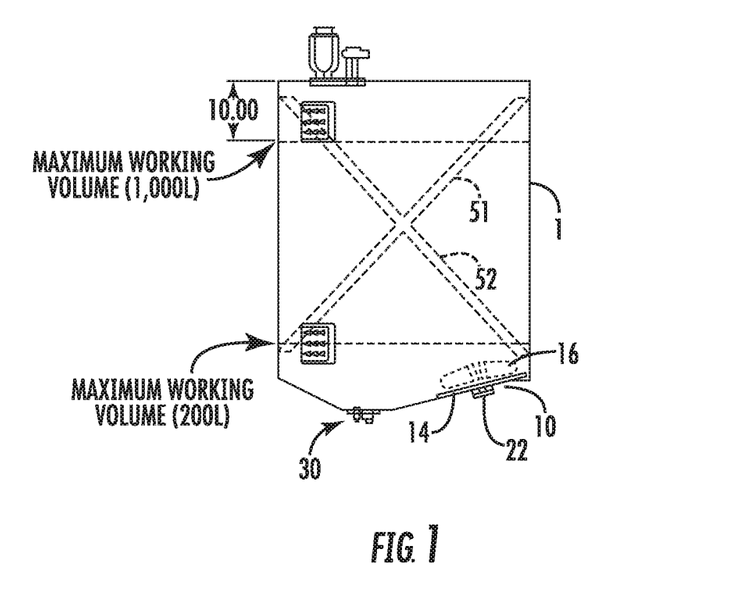
FIG. 1 is a cross-sectional view of a container having a baffle in accordance with certain embodiments.

Turning now to FIG. 1, there is shown a container 1 having an impeller assembly 10 having a base 14, and one or more moveable blades or vanes 16. The number and shape of the blades 16 is not particularly limited, provided they provide sufficient agitation of the fluid within the container when actuated. The base and blade or blades may be constructed of plastic material, such as polyethylene, or any polymer resistant to gamma irradiation, such as a polypropylene co-polymer. In certain embodiments, the base 14 includes an axially extending member 22 that accommodates the magnetic base of the impeller, such as a mixing impeller overmolded magnet, wherein the blades 16 extend axially above the member 22 where they are free to rotate when the magnetic impeller is drive by a drive magnet. In certain embodiments, when the impeller assembly 10 is installed in the disposable container 1, the extending member 22 protrudes outside the container 1 and it and/or the base 14 is sealed to the container 1. The remainder of the impeller assembly 10 is housed inside the container 1. Preferably the impeller assembly is positioned at or near the bottom of the container, when the container is in mixing position (such as a hanging position) and in close proximity to an inlet 30 of the container.

In the embodiment shown in FIG. 1, the disposable container 1 is made of weldable plastic such as polyethylene, and is sealed. Fluid access into the interior of the container 1 is via an inlet 30 that is sealed to a first conduit (not shown), and fluid access out of said container is via an outlet that is sealed to a second conduit (not shown). In certain embodiments, the container 1 has a minimum working volume of 200 L, and a maximum working volume of 1000 L. In certain embodiments, at least a portion of the impeller assembly is internal to the container, and the driver for the impeller assembly is external to the container 1.

Relatively short mixing times with homogeneous dispersion have been demonstrated even at the challenging points of 0.2:1 aspect ratio and high volumes up to 2000 L.

Figure 2:
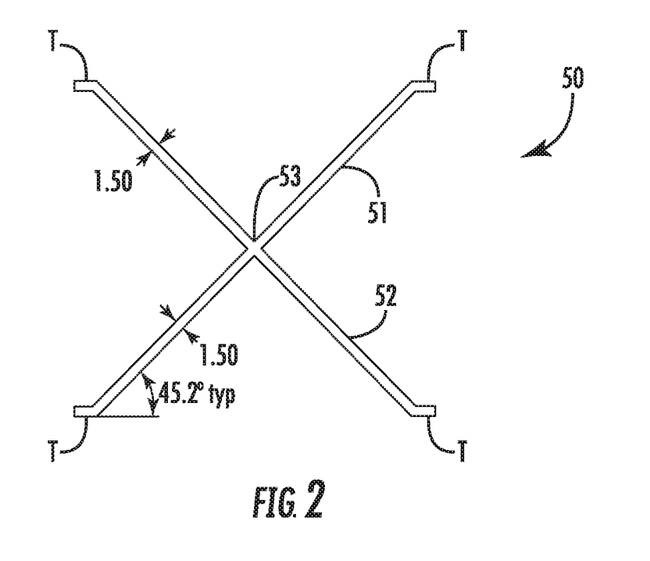
FIG. 2 is a cross-sectional view of a baffle in accordance with certain embodiments.

FIG. 2 illustrates an embodiment of the baffle 50. In certain embodiments, the baffle is a film made of weldable plastic such as polyethylene. The baffle 50 includes a first leg 51 and a second leg 52 that intersects and optionally attaches to the first leg 51. In certain embodiments, the location of the attachment of the legs 51 and 52 is at the longitudinal midpoint 53 of both legs. However, it is not necessary that the two legs actually contact or attach to one another. Each terminal end T of each leg is preferably bent at about a 45° angle with respect to the main body of each leg.

Each of these terminal ends can be affixed to the internal wall of the container, such as by welding, to affix the baffle in place in the container 1. In certain embodiments, where the container is a bag, the terminal ends are heat sealed within the seams of the bag. As exemplified in FIG. 2, in certain embodiments, these seams line up behind the impeller (12 o'clock) and across the bag at 6 o'clock. The bottom is attached at the lowest level of the bag and the top at a level that is above the maximum volume of the bag. Other attachment locations are possible, including attaching the baffle directly to the base of the system that supports the container, and/or to the top of the container instead of the sides. Indeed, doing so may introduce "slack" in the baffle, which may be acceptable. Regardless of the particular attachment locations, it is preferred that the upper legs extend out of the fluid, i.e., above the maximum volume of the bag (as opposed to being fully immersed in the fluid). This reduces mixing time by about 50%.

Figure 3:
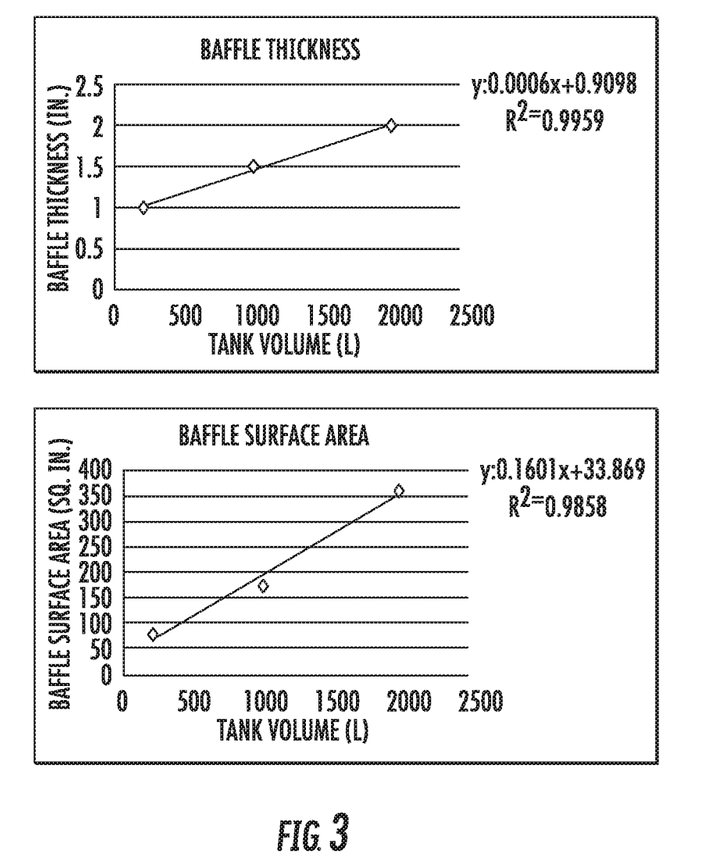
FIG. 3 is a graph of baffle thickness versus container volume, in accordance with certain embodiments, and a graph of baffle surface area versus container column, in accordance with certain embodiments.

The particular dimensions of the baffle depend at least in part on the size of the container. As shown in FIG. 3, baffle thickness is proportional to container volume, and is related to container volume by the equation $y=0.0006x+0.9098$ ($R^2=0.9959$). Similarly, baffle surface area is proportional to container volume, and is related to container volume by the equation $y=0.1601x+33.869$ ($R^2=0.9858$).

Preferably the baffle is placed in the container such that it extends through the vortex (or the region where the vortex would form in the absence of the baffle) at some level. The position of the vortex changes with aspect ratio. The region where the vortex would form in the absence of the baffle can be determined from experience, or by mixing fluid in the container under similar mixing conditions that will be used in operation, but in the absence of the baffle, and noting where the vortex forms. A "vortex map" can be created, documenting the location of the vortex for a given container aspect ratio, container volume, impeller position and impeller size. For an aspect ratio of 1:1 in a 1000 L container, the vortex is generally located at the 6 o'clock position. For an aspect ratio of 2:1 in a 2000 L container, and for an aspect ratio of 1.6:1 in a 200 L container, the vortex is generally located at the 9 o'clock position.

Although "X"-shaped baffles properly positioned in the container provide relatively low mixing times with homogenous mixing, other shapes are also suitable, provided the baffle intersects the region of vortex formation. Suitable shapes include zig-zag, triangle and diagonal baffles.

Example 1

Figure 4:
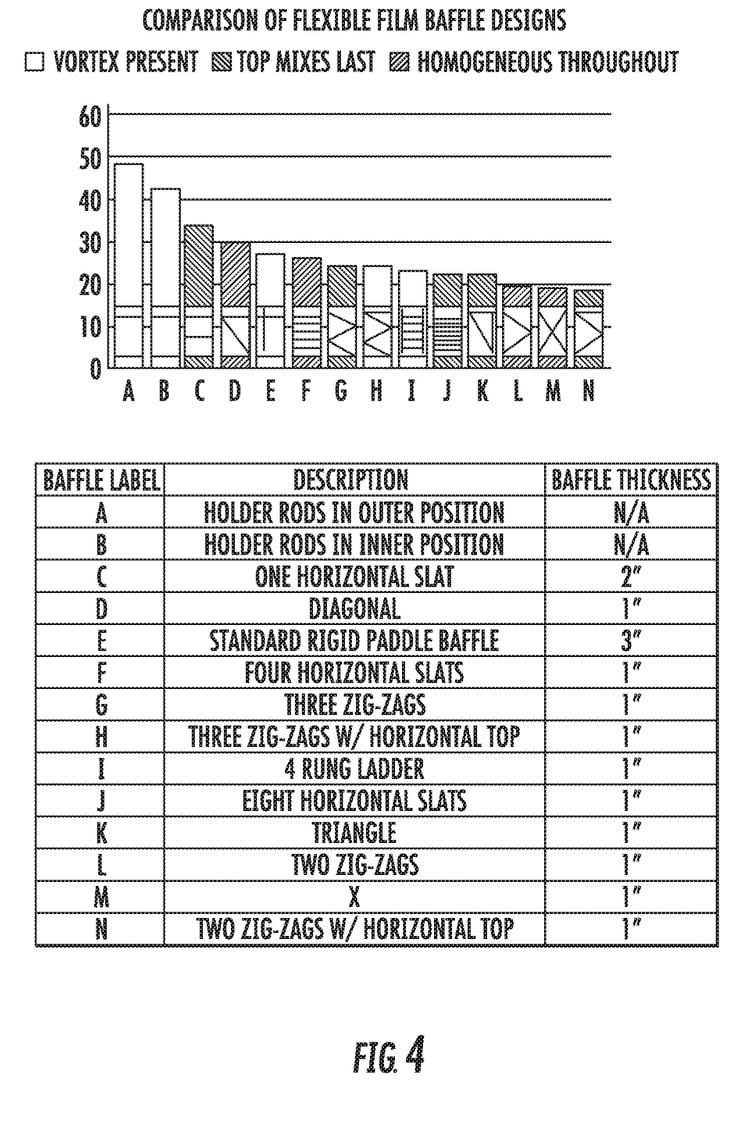
FIG. 4 is a chart of various baffle designs showing mixing times.

Mixing time and quality of produced by a sample of flexible baffles in a full 200 L tank were evaluated, with the results shown in FIGS. 4. A and B represent the metal rods that hold the film baffle in place inside the tank. These were run as controls to ensure that any effects on mixing were caused by the baffles and not the holders. E represents the standard rigid paddle baffle.

Table 2 shows the baffle thicknesses used in each of the samples in FIG. 4. Most of the baffles eliminated the vortex, but mixing times varied widely. The X-shaped baffled had the lowest mixing time with homogeneous mixing.

Example 2

This example was carried out to characterize the mixing performance for a bioreactor with a 13" impeller and X-shaped baffle to determine how changes in power input affect mixing performance and to determine the effectiveness of the impeller/baffle design across the range of volumes from 200 L to 2000 L.

Parameters for typical bioprocesses often include specifications for temperature, oxygen level, pH, and power input, among other factors. Power input is generally increased to enhance mixing performance. However, as power input is increased, the risk of cell damage due to shear can also be increased. To fully understand the capabilities of a bioreactor system, it is useful to understand the relationship between mixing time and power input, so as to allow the end user to optimize process conditions to best meet the needs of their particular cell line.

Testing was carried out to characterize mixing performance under a wide variety of conditions with a broad selection of equipment. Based on this testing, one of the designs chosen was based on a 13" 4-bladed impeller, with an X-shaped baffle.

Characterization of this design includes measurement of mixing time across power inputs from below 10 W/m³ to the maximum of 30 W/m$^3$, at the volume of 1000 L. In addition, mixing time for varying volumes (at constant power of 10 W/m$^3$) was also recorded.

Phenolphthalein mixing studies were conducted to evaluate the effectiveness of mixing with the 13" impeller and an X-shaped baffle. Levitronix® control software was used to monitor impeller performance factors, including speed and drive currents. These data were used to calculate power at each rpm where tests were done, according to the following formula:

Power=Torque*Rotational Speed Torque=(Drive Current $A$+Drive Current $B$)/2*Torque Constant/100

Torque Constant defined by Levitronix® as 21.32 for LPS-4000 motor

Rotational speed=2*3.14/60*rpm

By using a Phenolphthalein indicator, it is possible to observe mixing patterns as additions of acid and base change the pH or the liquid in the vessels. Mixing time is defined as the time for complete color change throughout the entire volume. The phenolphthalein (phth) mixing method was employed to obtain visual, colorimetric information about the mixing time and quality. This protocol is outlined as follows:

Materials:
  Phenolphthalein solution: 0.5% by wt. 1 L phth solution=5 g phth+600 mL ethanol+remaining volume DI water
  6M sodium hydroxide (NaOH)
  5M hydrochloric acid (HCl)
  DI water
  Timer with seconds indicator
  Video capability
  pH meter to monitor pH.

Methods: 1. Fill tank to desired volume with water. For each 100 L of water in the tank add 21 mL of phth solution.
  2. Turn the mixer on to ensure a homogeneous environment in the tank, then take a sample of the water and measure pH.
  3. Add acid/base to adjust the pH level to about 6.9.
  4. Turn video on. For each 100 L of water in the tank add 4 mL of 6M NaOH (turns solution pink).
  5. While the tank mixes, observe mixing patterns as solution changes color and note any zonal effects observed. Record the time it takes to achieve complete mixing (video playback can be used to more accurately record this time). Turn video off.
  6. Let the tank mix for an additional minute or so to ensure a homogeneous environment. Turn video on. For each 100 L of water in the tank add 3.4 mL of 5M HCl (turns solution clear).
  7. Repeat step 5.

NOTE: This process is repeatable for multiple trials. However, the pH should be periodically checked to make sure operation is in the window of about 6.9 to 8.5 (color change occurs at pH=8.2). Adjust the bulk pH as necessary. After some amount of time, the tank may reach its buffering capacity and it will be necessary to drain the tank and start again.

TABLE 3

Volumes of phth, acid, and base necessary for common volumes used in these mixing studies:

| Tank Volume | Volume of phth (mL) | Volume of 6M NaOH (mL) | Volume of 5M HCl (mL) |
|---|---|---|---|
| 200 L | 42 | 8 | 6.7 |
| 1000 L | 210 | 40 | 34 |
| 2000 L | 420 | 80 | 68 |

In most cases, the data are an average of 3 trials with a confidence interval of one standard deviation.

Figure 5:
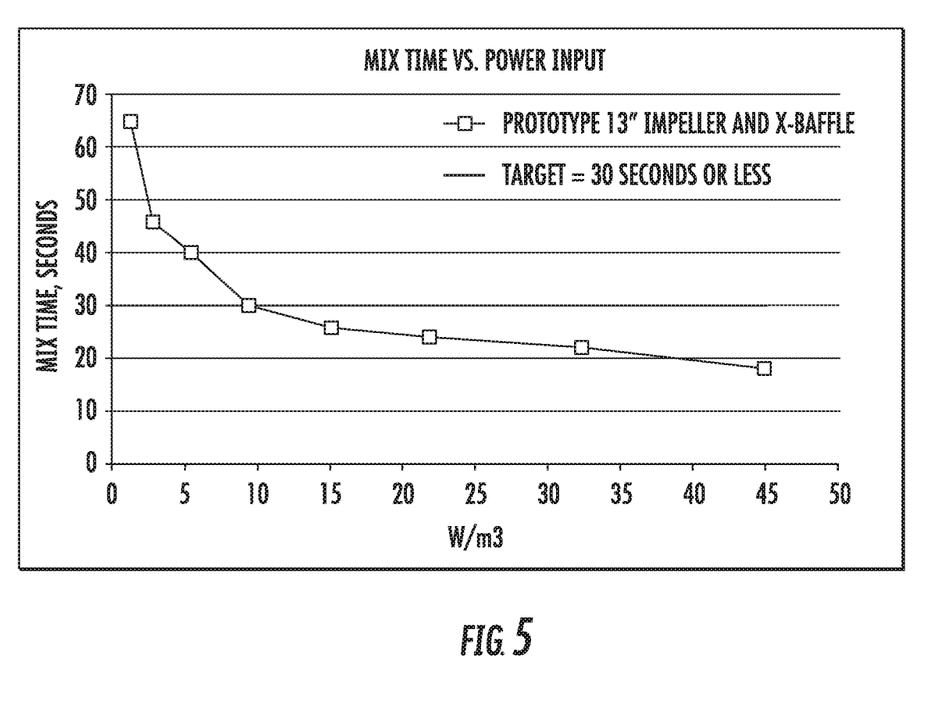
FIG. 5 is a response curve relating mixing time to power input.

The response curve relating mixing time to power input for a 13" impeller and X-shaped baffle at 1000 L is shown in FIG. 5. This curve clearly shows that the target of mixing time for 30 seconds or less is met for power input of 10 W/m$^3$ and greater. At all conditions, the addition of the X-baffle creates homogenous mixing.

Example 3

Figure 6:
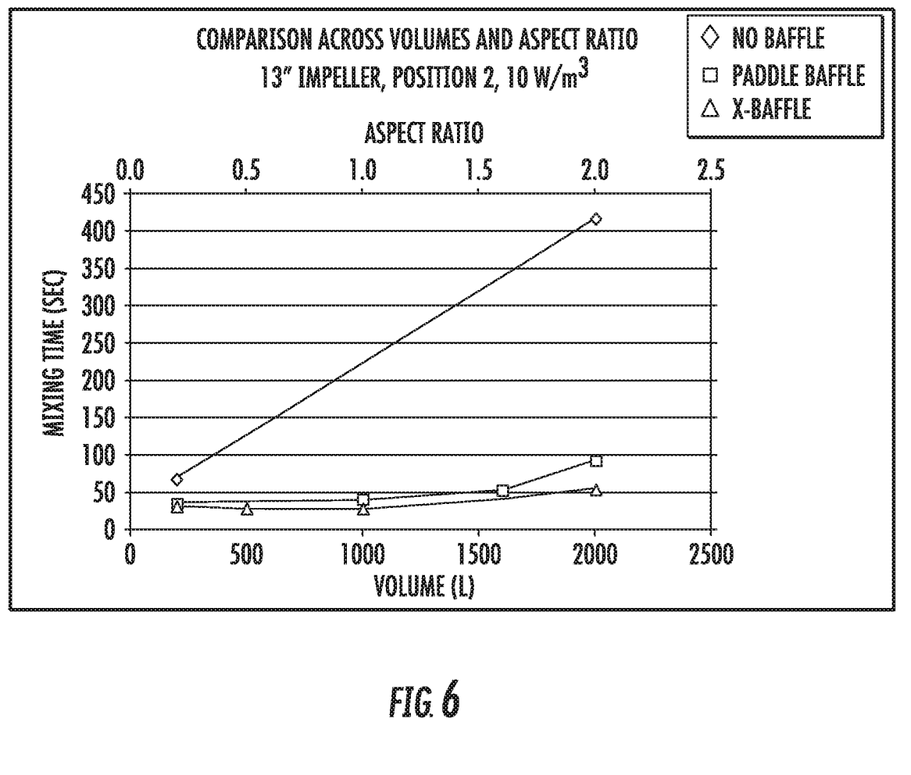
FIG. 6 is graph showing the performance of three systems (no baffle, paddle baffle, X-baffle) across volumes from 200 L to 2000 L.

A second series of characterization trials looked at the effectiveness of the X-shaped baffle across the full range of volumes from 200 L to 2000 L. With tank diameter constant, the change in volume corresponds to a change in aspect ratio, with the lowest volume of 200 L at 0.2:1 and the highest of 2000 L at 2:1. The results in FIG. 6 demonstrate the effectiveness of the X-baffle across this entire range of aspect ratios, especially as compared to a traditional paddle baffle and no baffle.

Figure 7:
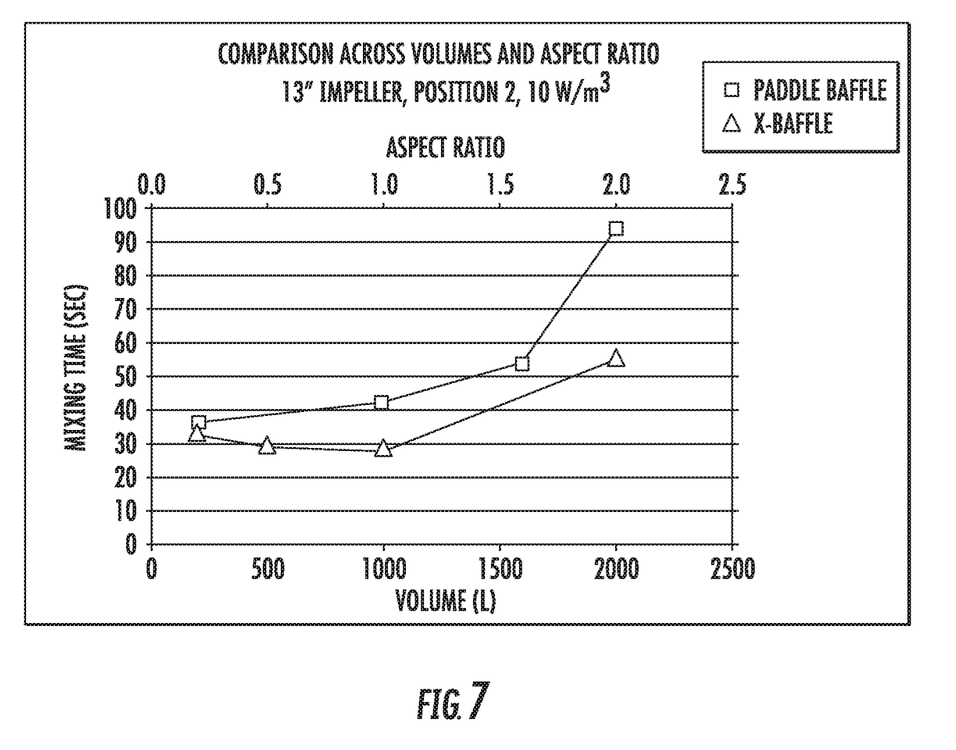
FIG. 7 is a graph of the comparison of a paddle baffle and an X-shaped baffle across volumes from 200 L to 2000 L.

FIG. 7 is a closer look at the data for just the systems with baffles. Here it is revealed that the X-baffle is less sensitive to increasing volume, with mixing time relatively constant at 30 seconds for all volumes from 200 L to 1000 L. This compares to the Paddle Baffle with mixing time at 200 L of 36 seconds, increasing by more than 15% to 42 seconds at 1000 L. At the highest volume of 2000 L, the value of the X-baffle is most apparent. With the paddle baffle, mixing time from 200 L to 2000 L increases by 145%, while the increase with the X-baffle is only 67%. The X-baffle provides a system with consistent mixing performance at both the lowest and highest aspect ratios.

The process window for this bioreactor could be opened as mixing time is under 30 seconds for power input as low as 10 W/m$^3$. The impeller/X-baffle design is at least effective from volumes of about 200 L to about 2000 L, with aspect ratios from about 0.2:1 to about 2:1.

What is claimed is:
1. A container for a fluid, comprising:
   a volume formed of a flexible material, the volume defined by a base, a top and at least one side connecting said top to said base, one or more inlets in said container, one or more outlets in said container, a fluid in said container having a fluid surface, an impeller assembly mounted at least partially within said volume of said container, said container having a height, and a flexible baffle in said volume of said container, said baffle being X-shaped when said container is viewed in cross-section from said top to said base, said X-shaped baffle being positioned in said container so as to have a horizontal and a vertical component in said container, said X-shaped baffle formed of two legs, each of said legs extending from a lower portion of said container to an upper portion of said container so as to form a diagonal with respect to the horizontal and slicing through said fluid surface and being only partially submerged in said fluid so as to enhance disruption of a vortex across the entire container height during operation of said impeller assembly to mix said fluid.

2. The container of claim 1, wherein said volume is a closed volume.

3. The container of claim 1, wherein said container is bioreactor.

4. The container of claim 1, wherein said fluid comprises cells.

5. The container of claim 4, wherein said fluid further comprises microcarriers for said cells.

6. The container of claim 1, wherein said container has an internal wall, and wherein said baffle extends to said internal wall.

7. The container of claim 1, wherein said baffle has a thickness that is related to said volume of said container by the relationship: baffle thickness (inches)=0.0006*(tank volume (liters)+0.9098.

8. The container of claim 1, wherein said baffle has a surface area that is related to said volume of said container by the relationship: baffle surface area (square inches)= 0.1601*(tank volume (liters)+33.869.

9. A method of mixing a fluid in a container, comprising:
providing a container defining a volume and having a height, the volume defined by a base, a top and at least one side connecting said top to said base;
providing an impeller assembly mounted at least partially within said volume of said container;
positioning a flexible baffle in said volume of said container so as to have a horizontal and a vertical component in said container; said baffle being X-shaped when said container is viewed in cross-section from said top to said base, said X-shaped baffle formed of two legs, each of said legs extending from a lower portion of said container to an upper portion of said container so as to form a diagonal with respect to the horizontal,
introducing fluid to be mixed into said container to a level only partially submerging said baffle, thereby defining a fluid surface, wherein each of said legs slices slicing through said fluid surface; and
driving said impeller assembly to mix said fluid;
whereby said baffle minimizes the formation of any vortex across the entire container height during said mixing.

10. The method of claim 9, wherein said container is a bioreactor.

11. The method of claim 9, wherein said fluid comprises cells.

12. The method of claim 11, wherein said fluid further comprises microcarriers for said cells.

13. The method of claim 9, wherein said container has an internal wall, and wherein said baffle is positioned in said volume of said container to extend to said internal wall.

14. The method of claim 9, wherein said baffle has a thickness that is related to said volume of said container by the relationship: baffle thickness (inches)=0.0006*(tank volume (liters)+0.9098.

15. The method of claim 9, wherein said baffle has a surface area that is related to said volume of said container by the relationship: baffle surface area (square inches)= 0.1601*(tank volume (liters)+33.869.

* * * * *